United States Patent
Tessarek

(10) Patent No.: US 11,931,240 B2
(45) Date of Patent: Mar. 19, 2024

(54) MULTILUMEN IMPLANT

(71) Applicant: Stental GmbH, Lörrach (DE)

(72) Inventor: Jörg Tessarek, Lingen (DE)

(73) Assignee: Stental GmbH, Lörrach (DE)

( * ) Notice: Subject to any disclaimer, the term of this patent is extended or adjusted under 35 U.S.C. 154(b) by 0 days.

(21) Appl. No.: 17/054,967

(22) PCT Filed: May 15, 2019

(86) PCT No.: PCT/EP2019/062431
§ 371 (c)(1),
(2) Date: Nov. 12, 2020

(87) PCT Pub. No.: WO2019/219728
PCT Pub. Date: Nov. 21, 2019

(65) Prior Publication Data
US 2021/0236261 A1    Aug. 5, 2021

(30) Foreign Application Priority Data

May 15, 2018    (DE) ..................... 10 2018 111 614.4

(51) Int. Cl.
*A61F 2/07*    (2013.01)
*A61F 2/954*    (2013.01)

(52) U.S. Cl.
CPC .............. *A61F 2/07* (2013.01); *A61F 2/954* (2013.01); *A61F 2002/072* (2013.01); *A61F 2210/0014* (2013.01); *A61F 2220/0016* (2013.01); *A61F 2220/0075* (2013.01); *A61F 2240/001* (2013.01); *A61F 2250/006* (2013.01); *A61F 2250/0081* (2013.01)

(58) Field of Classification Search
CPC ............ A61F 2/07–2002/077; A61F 2250/006
See application file for complete search history.

(56) References Cited

U.S. PATENT DOCUMENTS

| 5,667,523 A | * | 9/1997 | Bynon | ....................... A61F 2/07 606/194 |
| 6,315,791 B1 | * | 11/2001 | Gingras | ..................... A61F 2/06 623/1.13 |
| 2003/0065385 A1 | | 4/2003 | Weadock | |
| 2003/0114918 A1 | * | 6/2003 | Garrison | ................... A61F 2/90 623/1.13 |
| 2003/0176911 A1 | | 9/2003 | Iancea | |

(Continued)

FOREIGN PATENT DOCUMENTS

WO    WO2018/091442 A1    5/2018

*Primary Examiner* — Rebecca S Preston
(74) *Attorney, Agent, or Firm* — Brooks Kushman P.C.

(57) ABSTRACT

Multilumen implant for application in human and animal vascular systems/bodies, with a substantially tubular element (1) divided into a proximal (2) and a distal section (3), and a fixation element (8) for the fixation of the proximal section (2) in a target vessel, wherein the tubular element (1) branches into two or more lumens (4, 5) in the distal section (3), with the fixation element (8) being at least one clamping ring (8) arranged on the outside of the proximal section (2) of the tubular element (1), and wherein the free end of the proximal section of the tubular element (1) is folded around the clamping ring (8) and embraces the clamping ring (8) in a pocket-like manner.

14 Claims, 10 Drawing Sheets

(56) References Cited

U.S. PATENT DOCUMENTS

| | | | | |
|---|---|---|---|---|
| 2005/0010277 A1* | 1/2005 | Chuter | ............... | A61F 2/064 623/1.13 |
| 2007/0038288 A1* | 2/2007 | Lye | ............... | A61F 2/07 623/1.16 |
| 2007/0156228 A1* | 7/2007 | Majercak | ............... | A61F 2/07 623/1.13 |
| 2013/0041456 A1* | 2/2013 | Greenberg | ............... | A61F 2/07 623/1.35 |
| 2014/0277348 A1* | 9/2014 | Roeder | ............... | A61F 2/07 623/1.11 |
| 2015/0320578 A1* | 11/2015 | Bui | ............... | A61F 2/856 623/1.35 |

* cited by examiner

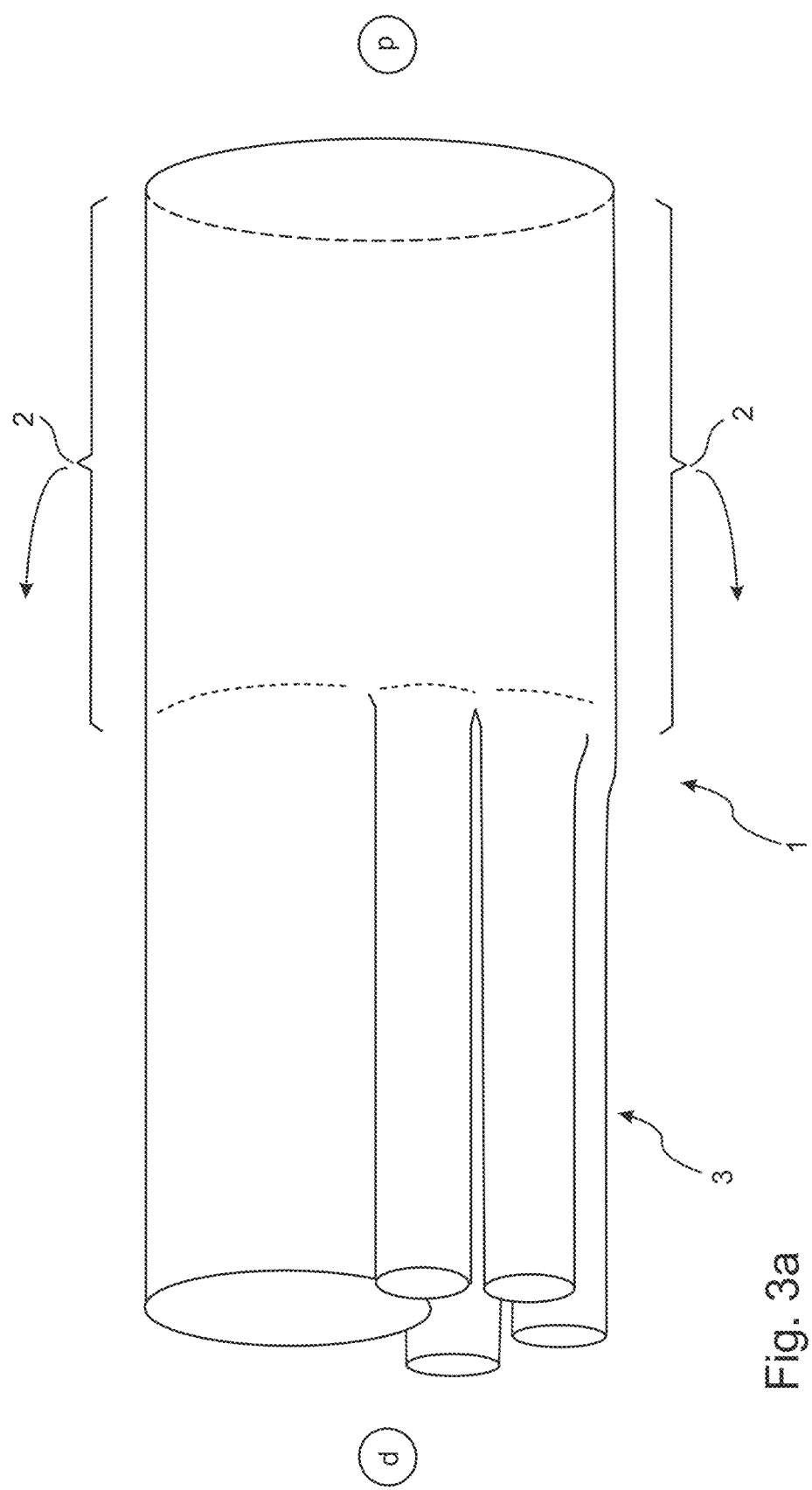

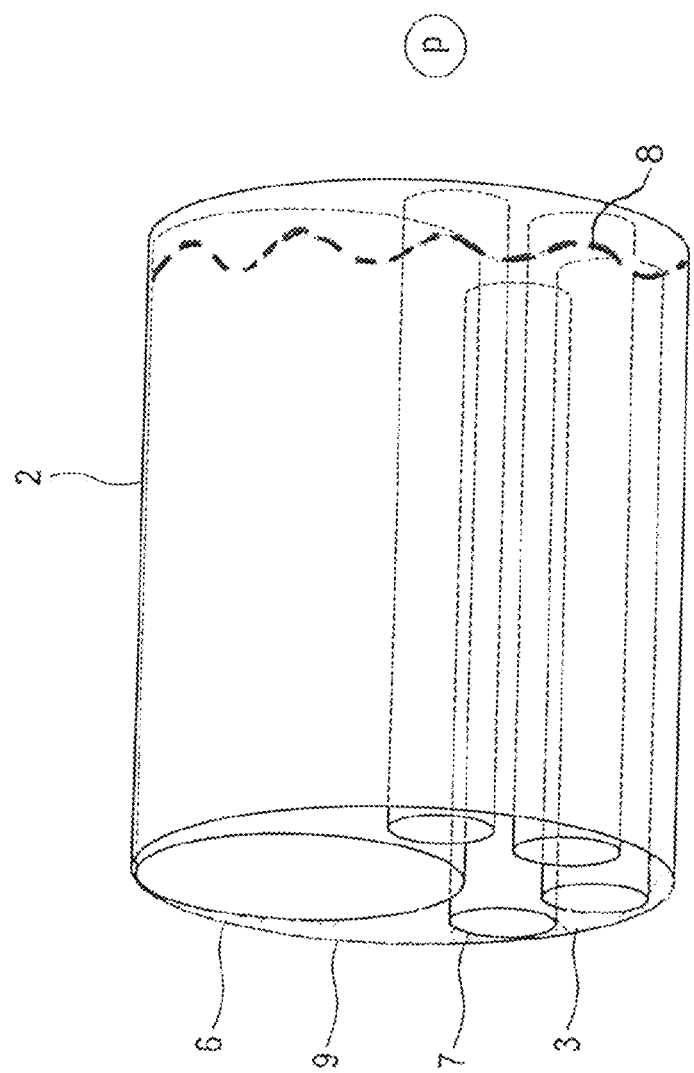

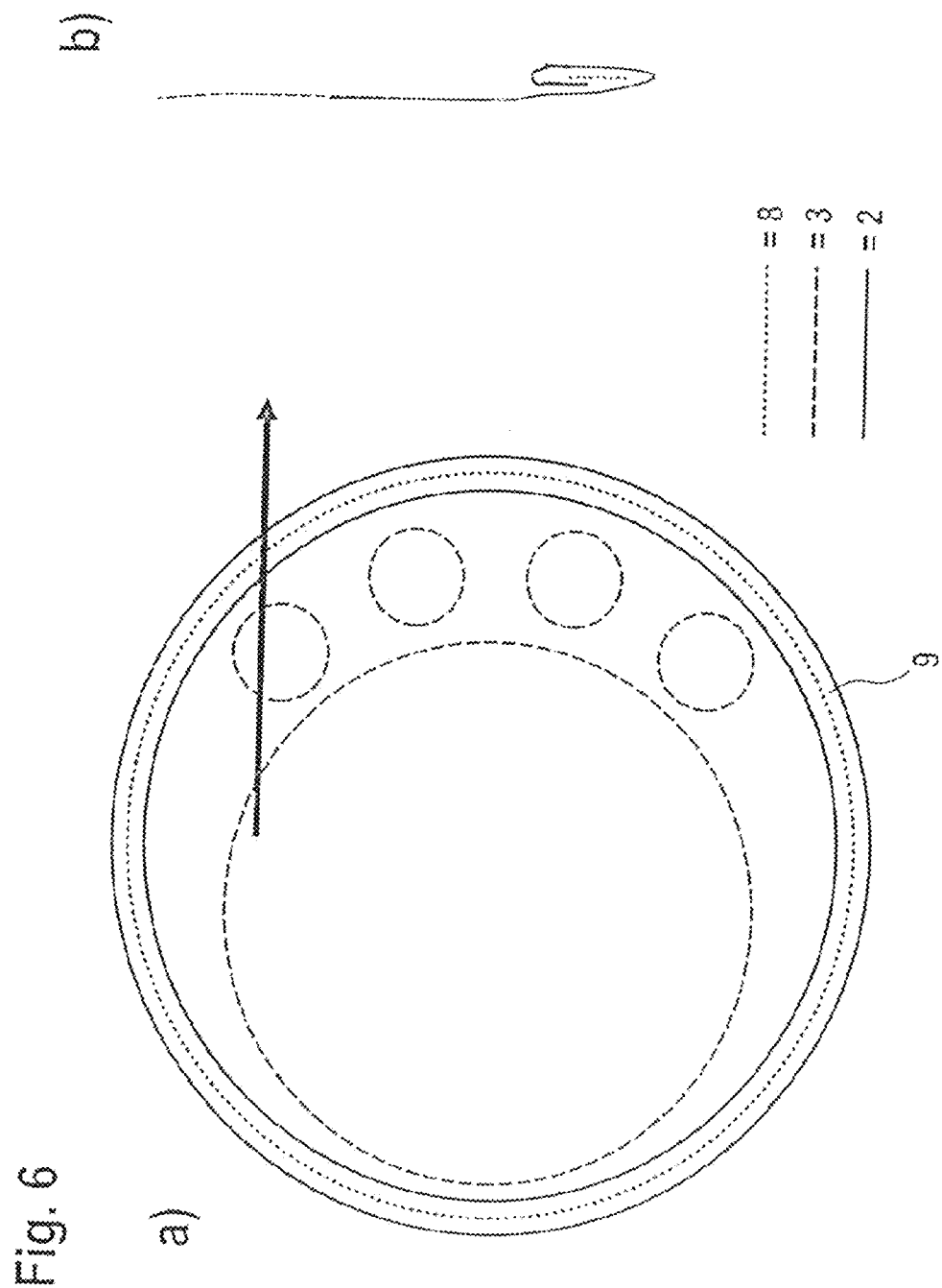

MULTILUMEN IMPLANT

The invention relates to a multilumen implant for application in human and animal vascular systems, comprising a substantially tubular element divided into a proximal and a distal section, and at least one fixation element for the retention of the proximal section in a target vessel, wherein the tubular element branches into two or more lumens in the distal section, wherein the fixation element is a clamping ring arranged on the outside of the proximal section of the tubular element, and wherein the free end of the proximal section of the tubular element is wrapped around the clamping ring and embraces the clamping ring in a pocket-like manner.

Aneurysms are one of the most common pathologies of the human vascular system. Aneurysms are protuberances or bulges occurring in the vascular wall. The specific causes may be of a very different nature, but it can be said in general that the affected part of the vessel wall is weakened initially and afterwards widens more and more due to the constant blood pressure acting on it.

Generally speaking, aneurysms may occur in all regions of the body and in all locations of the vessel system. However, there are certain parts of the human body that are predestined for the formation of aneurysms simply because of their vascular anatomy. This includes, for example, all vascular branching locations, so-called bifurcations.

There are two aspects concerning the danger that an aneurysm poses to the patient's health. On the one hand, the aneurysm itself can lead to problems if it exerts pressure on other vessels or organs, for example. This may cause pain and/or result in an undersupply of other parts of the body and organs. For instance, if the brain is affected, more or less severe neurological deficits are the result.

On the other hand, a rupture of the aneurysm may take place, that is, aneurysms can also tear open. This is particularly dangerous for the patient if the aneurysm is situated in the brain or on a large vessel that is carrying or conducting a great volume of blood. Brain hemorrhage may be caused in the event burst aneurysms occur in the brain, which may result in mild to most severe neurological damage depending on the size of the vessel and the severity of the bleeding, and in the worst case, such a brain hemorrhage may even lead to the death of the patient. If an aneurysm tears on a large vessel in the patient's body, fatal blood loss can occur within a very short time, for example in the event of ruptures of abdominal artery aneurysms or thoracic aneurysms.

Until a few years ago, many aneurysms required an open surgical treatment but, meanwhile, a wide range of alternative treatment options and medical devices is now available for the minimally invasive and intravascular treatment of aneurysms.

One of the preferred minimally invasive, intravascular aneurysm treatment options is the placement of stent grafts. A stent graft comprises a stent framework and a covering, which when combined results in an implant of tubular shape. For the treatment of an aneurysm, such a stent graft bridges the area of the aneurysm by connecting the healthy portions of the vessel via the stent graft, causing the blood in the area of the aneurysm to pass through the stent graft. On the one hand, a rupture of the aneurysm is thus prevented and, on the other, the pressure that the aneurysm has exerted on other structures is largely eliminated as blood is no longer allowed to pass through the aneurysm.

The placement of such a stent graft in the form of a simple tubular element becomes particularly problematic when lateral branches leave the affected vessel in the area of the aneurysm. In this case, the implantation of a stent graft causes the lateral branches in this area to be also cut off from the blood supply, just like the aneurysm itself. Accordingly, the areas and/or organs to be perfused via the side branches are cut off from the blood supply.

In order not to cut off the side branches from the flow of blood, it is necessary to supply them via stent graft conduits/leads. In the state of the art, a large number of techniques are known that offer possible solutions. Today, it is primarily custom-made or modular implants that have established themselves, which are tailored to the needs of each individual patient. Such custom-made products and also modular systems are expensive. Manufacturing special custom-made products is time consuming, as they usually have to be made individually by hand. Modular systems, on the other hand, are quite frequently assembled by the surgeon in the patient in the course of the intervention.

For example, publication EP 2 749 251 B1 (Cook Medical Technologies LLC) discloses an extendable stent graft consisting of a base body and rings that is capable of being modularly adapted in a certain manner to the respective vessel anatomy. And EP 2 081 515 B1 (Cook Medical Technologies LLC) discloses a special window arrangement in stent grafts so as to be able to connect lateral branches to the implant as universally as possible. In addition, publication WO 2014/197743 A1 (Aortic Innovations Surena LLC) claims a variable stent graft system, the modular design of which allows the diverting lateral branches of the implant to be adapted to the vascular anatomy of the patient in predetermined longitudinal paths.

All these systems are associated with disadvantages. As a rule, implantation requires an experienced surgeon, in many cases even system-related training is necessary in order to construct the modularly designed implants correctly in the patient's body in the course of the intervention.

Fixation of the main lumen via stents also has the disadvantage that the implant requires a great amount of space in the non-expanded state, which makes placement through a catheter particularly difficult, also due to increased friction. In general, large catheter calibers are required for the placement of such implants.

Moreover, an implantation of custom-made, i.e. tailored systems also presents the surgeon with major challenges. The anatomically accurate adaptation of the implant to the main branch and the accesses to the lateral branches require the surgeon to fit the implant very precisely into the patient's anatomy. What appears to be quite simple in the rigid model is in practice a very difficult undertaking, because the vessels are not at all rigid and may change their position relative to each other.

The consequences of using such complex systems, whether they are completely assembled or of modular design, are a sometimes long and thus stressful intervention duration for the patient and the surgical team, and, what is more, an increasing probability of device failures.

Moreover, the state-of-the-art systems usually have to be completely implanted in the course of a single intervention. A step-by-step implantation, whether planned or as a reaction to the patient's condition, is ruled out in all probability, or at least not without risk, because only a completely implanted system will produce the desired result. Due to this, the surgeon can hardly react, for example, to a worsening condition of the patient during the intervention by postponing partial steps to a later date. Similarly, it is normally impossible from the beginning to perform planning of the intervention to take place over several days.

Also, the access possibilities that known systems offer are often limited as a result of their design configuration. Due to their complexity, these systems as a rule have quite large diameters even when in folded state and, consequently, need to be inserted only through correspondingly large introducer sheaths. Usually, this prevents the system to be introduced via the arm. Likewise, a retrograde access, for example to connect the lateral branches, is usually impossible with known systems for design-related reasons.

Another disadvantage of the prior-art systems is that they may develop a leak, a so-called endoleak, through migration (displacement of the prosthesis), texture damage or the progression of the disease in the upper and lower sealing segment. Relevant remedial action can be extremely sophisticated and as a rule can only be performed by open surgery.

Another decisive disadvantage of the prior-art systems is that they need to be tailored to the specific situations. The prior-art systems, even if they are of partially modular design, must in most cases still be made by hand to suit the requirements of the specific case. Usually, this takes days or even weeks and in exceptional cases may require several months before they are available. More often than not, emergency care with such implants is therefore not possible, which may lead to the avoidable death of a patient within the waiting period for an appropriate implant.

It is therefore an objective of the present invention to provide a multilumen implant that is suitable for the treatment of a plurality of patients and a variety of clinical pictures due to its universal application and connection possibilities, without the need for pre-interventional tailoring or individualization. Such a system is also suitable for emergencies and can be stored in hospitals so as to be readily available.

Another objective of the present invention is the provision of a multilumen implant having an as small a diameter as possible in the folded state, which can be introduced accordingly via an introducer sheath of small diameter, so that aside from femoral accesses, in particular arm accesses can also be used as standard procedure.

It is moreover the objective of this invention to provide a multilumen implant that is compatible with customarily available accessories. In particular, it should be possible to use as many of the available prior-art covered stents and stent grafts as possible with a view to connecting the implant to the continuing vascular system. Similarly, stepwise interventions should also be made possible.

Still another objective of the invention is to provide a system that can be designed in an as simple as possible manner and is very easily implanted. This minimizes both the costs and failure rates of the system as well as the duration and risks of interventions.

It is also the task of the invention to provide an implant that is suitable for taking remedial action on prior-art systems in the event of a defect, by providing a seal that is completely independent of the original system and offering its own anchoring method, so that already placed prosthetic components, for example of an endograft, can remain in the body.

With a view to attaining the objectives called for, the implant proposed by the invention pursues an approach which differs conceptually clearly from that of prior-art implants. Prior-art implants attempt to reproduce the anatomy of the damaged vascular region, so to speak try to provide a lining of the region to be repaired. Accordingly and as described hereinbefore, these implants must be individually fabricated and implanted as accurately as possible. On the other hand, an inventive implant is to be viewed as a kind of distributor insert, in principle, the lumen of which can be individually connected to the vessels to be treated using covered stents.

This objective is achieved by a multilumen implant comprising the characteristics of claim 1. Advantageous embodiments in each case are the subject of the dependent claims. It is to be noted that any features and characteristics individually included in the claims may also be combined with each other in an optional and technologically sensible manner so that they reveal further implementations or methods of the invention.

The implant proposed by the present invention can be used as an interlocking device, particularly in the thoracoabdominal and iliac region.

In a first embodiment of the invention proposed the implant consists of a substantially tubular element and a clamping ring for the fixation of the tubular element in a vessel.

The tubular element is structured to form a proximal and a distal section, with the distal section branching into at least two lumina. In the present application, the term distal always denotes the part of a structure that points in the direction of the blood flow, so that, correspondingly, the term proximal denotes the part that faces against the direction of the blood flow.

The tubular element can be imagined as and compares to a kind of glove. In such a comparison, the proximal section of the tubular element corresponds substantially to the part of the glove surrounding the palm of the hand while the distal portion of the tubular element substantially corresponds to the fingers of the glove, with the distal branches of the implant that correspond to the fingers ending openly or being openable at their ends.

In a preferred embodiment, the proximal lumen branches distally into five lumens, one main lumen and four secondary lumens, but other subdivisions are easily conceivable and can be realized without difficulty. The implant proposed by the invention is in no way limited to embodiments which resemble the proportions, dimensions or other characteristics of a finger glove.

The tubular element is secured by means of one or several clamping rings on the inside or outside of the proximal section of the tubular element upstream of the aneurysm in the target vessel. The tubular element may be attached to the one or several clamping rings by further measures, for example by clamping, welding, bonding, sewing or other known techniques. Preferred is a clamp-like connection, as it has been disclosed in publication WO 2012/084202 A2. Sewing at least one clamping ring into the folding formed by the tubular element is particularly preferred.

The clamping ring or rings are arranged in the proximal area of the tubular element. At least one clamping ring is located on the outside—the side facing the vessel wall—of the tubular element and is enclosed in a pocket-like cover formed by the outwardly folded free end. The clamping ring can be sewn into this pocket. This design offers an advantage in that the pressure the clamping ring exerts on the vessel wall is "cushioned".

The clamping ring itself has an undulating shape, whereby "undulating" means meandering or zigzagging. This enables the clamping ring to be extensively compressed for transporting the implant in a catheter and suitably expanded so as to adapt to the vessel caliber during placement. As provided by the invention, self-expanding clamping rings are preferred.

Compared to a stent, a clamping ring has the advantage of exerting greater radial force. In the event of a stent used for graft fixation, the radial force is distributed over the entire surface, whereas a clamping ring enables the force to be concentrated on the ring zone where contact is made with the vessel wall. When the correct diameter is selected, the undulated design of the clamping ring also allows its expansion within the vessel to be carried out in such a targeted manner that the greatest possible radial force is transmitted.

As provided by the invention, a clamping ring preferably consists of a closed wire ring, which is zigzag-shaped or wave-shaped. This allows compression within a catheter of small diameter and the implant's subsequent expansion when released from the catheter. Preferably, expansion takes place by the self-expansion of a shape memory material, such as a nickel-titanium alloy, but a balloon expandable material such as a spring steel alloy can also be employed. When using self-expanding materials, it is important that the clamping ring in the vessel has a residual expansion capacity that ensures the fixation of the multilumen implant in the vessel.

A ring cut from a tube with the help of a laser may also be used for the clamping ring. In this case, the same criteria apply as described above.

For example, the clamping ring has a diameter ranging between 0.15 and 0.80 mm, in particular between 0.40 and 0.60 mm. This applies both to clamping rings made of wire and to laser-cut rings.

The dimension of the clamping ring is therefore chosen such that it offers sufficient force to secure the implant to the vessel wall. In addition, a reserve should be available to cope with an enlargement of the surrounding vessel, for example due to ageing.

As provided by an embodiment of the invention, the multilumen implant comprises a clamping ring which is arranged on the outside in a folding or envelope of the tubular element. This clamping ring is preferably sewn in. This embodiment offers the advantage that the clamping ring has to some extent freedom of movement within the folding, which improves sliding in the catheter and placement in the vessel.

According to another embodiment of the invention, the multilumen implant is provided with two clamping rings, of which an outer one is placed on the outside within the folding of the tubular element and an inner one that is placed against it on the inside of the tubular element in the proximal section. It is advisable to connect the two clamping rings to each other through the tubular element, for example by sewing. Expediently, the undulations of the two clamping rings have a staggered arrangement, which results in a better fixation of the proximal part of the tubular element between the clamping rings and the multilumen implant on the vessel wall.

It goes without saying that two or more clamping rings can also be arranged in the implant in other ways, for example next to each other in the folding, or alternately in the folding and on the inside of the tubular element.

With respect to the fixation of the inventive implant in the vessel, fastening elements may also be provided, such as hooks or screws that extend into the vessel wall. Such fastening elements are known per se and are used clinically (Heli-FX EndoAnchor™). These fastening means can be hooks connected to the clamping ring, which engage in the vessel wall during expansion, or screw elements, which in the proximal area of the tubular element secure the element with the clamping ring at the vessel wall.

The distal section of the tubular element branches into at least two lumens, whereby the number of lumens is arbitrary and the number of branches may be selected, for example, to suit the number of vessels to be perfused. However, preferred are embodiments in which two or five branches are arranged.

Particularly preferred are embodiments comprising one main lumen having a larger diameter and four secondary lumens of smaller diameter. Nevertheless, the diameters are basically arbitrary and can be selected to suit the intended use of the implant. When using the implant in the thoracic and abdominal area, diameters of the proximal section may range between 5 and 45 mm, preferably between 20 and 42 mm, possible diameters for the main lumen range between 3 and 30 mm, preferably between 12 and 25 mm, and for the secondary lumens diameters between 2 and 12 mm, preferably between 4 and 10 mm, may be used. When it is intended to use the implant in the cerebral area, diameters of the proximal section may range between 2 and 15 mm, preferably between 2 and 8 mm, possible diameters for the main lumen range between 1 and 5 mm, preferably between 2 and 4 mm, and for the secondary lumens diameters between 1 and 4 mm, preferably between 2 and 3 mm, may be used. In the event the implant is to be applied in the coronary area, diameters of the proximal section may range between 2 and 8 mm, preferably between 4 and 6 mm, possible diameters for the main lumen range between 2 and 6 mm, preferably between 3 and 5 mm, and for the secondary lumens diameters between 2 and 5 mm, preferably between 2 and 3 mm, may be used.

Aside from the embodiments referred to above, it is also conceivable that embodiments may be provided with a total of more or less than five lumens, and, moreover, that the embodiments may have more than one main lumen and more or less than four secondary lumens.

If one thinks of a cross-section through an area of the implant after branching, it is preferred to make use of embodiments having an eccentric distribution of the lumens, in which case the branching with the largest lumen is located on one side and one or more branches of smaller lumens are arranged on the other side in the cross-sectional view. However, the distribution of the branches in the distal section of the tubular element is not predetermined, and it is also conceivable that embodiments can be used in which, for example, one branch is located in the central area and other branches are uniformly or unevenly distributed around the central lumen.

In a preferred embodiment, the individual branches have the same length, but other embodiments that provide for the branches to be of different lengths are also conceivable. On the whole, it is preferred if the branches terminate distally approximately with the folded over proximal end of the tubular element. It is conceivable, however, that, distally, the folded over proximal end of the tubular element also reaches over the branches or that the branches protrude distally from the folded over proximal end of the tubular element.

The branches of the implant are connected to the vessels located distally to the implant via covered stents, so-called stent grafts, resulting in bridging the aneurysm area in this manner thus preventing the flow of blood into the aneurysm and relieving pressure on the aneurysm. At the same time, the distally located vessels are purposefully supplied with blood via the stents.

For better fixation of the stents that connect the distal branches of the tubular element to the vessels each to be supplied with blood, the distal branches in a preferred embodiment may taper conically towards their end entirely or over a certain length of a respective branch.

Further measures to secure the stents in the distal branches are conceivable in the form of ring-shaped or other reinforcements or stiffeners, especially in the distal areas. On the one hand, this ensures the firm fit of the stent graft and due to this reinforcement also reduces the risk of tearing of the distal branches during the implantation of the stent grafts.

The branches in the distal section preferably run freely from each other, but embodiments are also conceivable that provide for some or all of the branches to be bonded together, if thought expedient also in groups. The branches may also be attached—additionally or alternatively—to the stent serving to secure the implant in place or to the folded-around proximal section of the tubular element.

As materials for the tubular element any physiologically compatible material known in the state of the art can be employed, primarily ePTFE, said materials may also be processed by electrospinning.

For the clamping ring, all materials known in the state of the art can be used that guarantee a permanent fixation of the tubular element and are not resorbable.

Typically, the implant proposed by the present invention is placed at the proximal end of the aneurysm in the still intact vascular section. In this case, the implant fulfils the function of a distribution disk or element that allows the blood to flow exclusively through the lumina of the distal branches. With a view to bridging the region of the aneurysm, the distal branches of the tubular element are connected via covered stents to the vessels located distally to the implant.

This technique makes it possible to also carry out the intervention step by step due to the fact that the placement of the implant initially does not prevent the flow of blood to the vessels situated distally to the implant. For example, in a first intervention the implant itself can thus be placed in position and in one or more subsequent interventions the vessels are connected.

A retrograde approach to connect the vessels and branches of the implant with each other is also possible, which is difficult or even impossible to achieve with prior-art implants.

As a result of its universal adaptability, the multilumen implant the invention proposes also enables repairs of already placed systems which have developed a leak, a so-called endoleak, due to migration (displacement of the prosthesis), texture damage or the progression of the disease in the upper and lower sealing segment. The already implanted prosthetic parts may remain in the body, because the multilumen implant has a completely independent sealing effect and its own anchoring system.

However, a variety of other advantages are offered by an implant according to the invention. They also relate to manufacturing costs and thus to health system expenses, patient safety, improved planning/scheduling, availability, product safety and also the safety of relevant interventions.

Due to its universal applicability, the implant can be produced in larger quantities at correspondingly lower unit costs due to standardization to preferably five distal lumina and is therefore significantly less expensive than individualized implants.

Since the implant can be used universally due to its flexible connection options, it can be stocked in the clinic and thus also used in acute emergencies. A specific tailored production associated with long waiting times is thus not necessary.

The implant is easy to implant, it does not need to be prefabricated or assembled in the patient's vascular system. Basically, implantation is carried out in the same way as the insertion of a normal stent. For the connection of the branches to the vessels no special knowledge is required either, it is similar to the routine placement of stent grafts.

In comparison with prior-art implants, the simplicity of the inventive implant also makes it less susceptible to device failures which may be encountered in the course of the intervention or be the result of previous fabrication, processing and preparation activities.

Last but not least, it is to be assumed that the safety aspects of the actual intervention will improve, since due to the simplicity of the intervention process—the complexity of connecting the vessels and the assembly of the implant in the patient are eliminated—the intervention time and thus automatically also the risk of surgery-related complications will be reduced.

The invention as well as the technical environment are described hereunder in sufficient detail on the basis of the figures. It is to be noted that the figures show an especially preferred embodiment variant of the invention. However, the invention shall not be deemed as being limited to the embodiment variant shown. To the extent it is technically expedient, the invention comprises, in particular, any optional combinations of the technical features that are stated in the claims and in the description and pertinent figures as being relevant to the invention.

Elucidation of the invention is provided by the following figures where

Figure 3B:
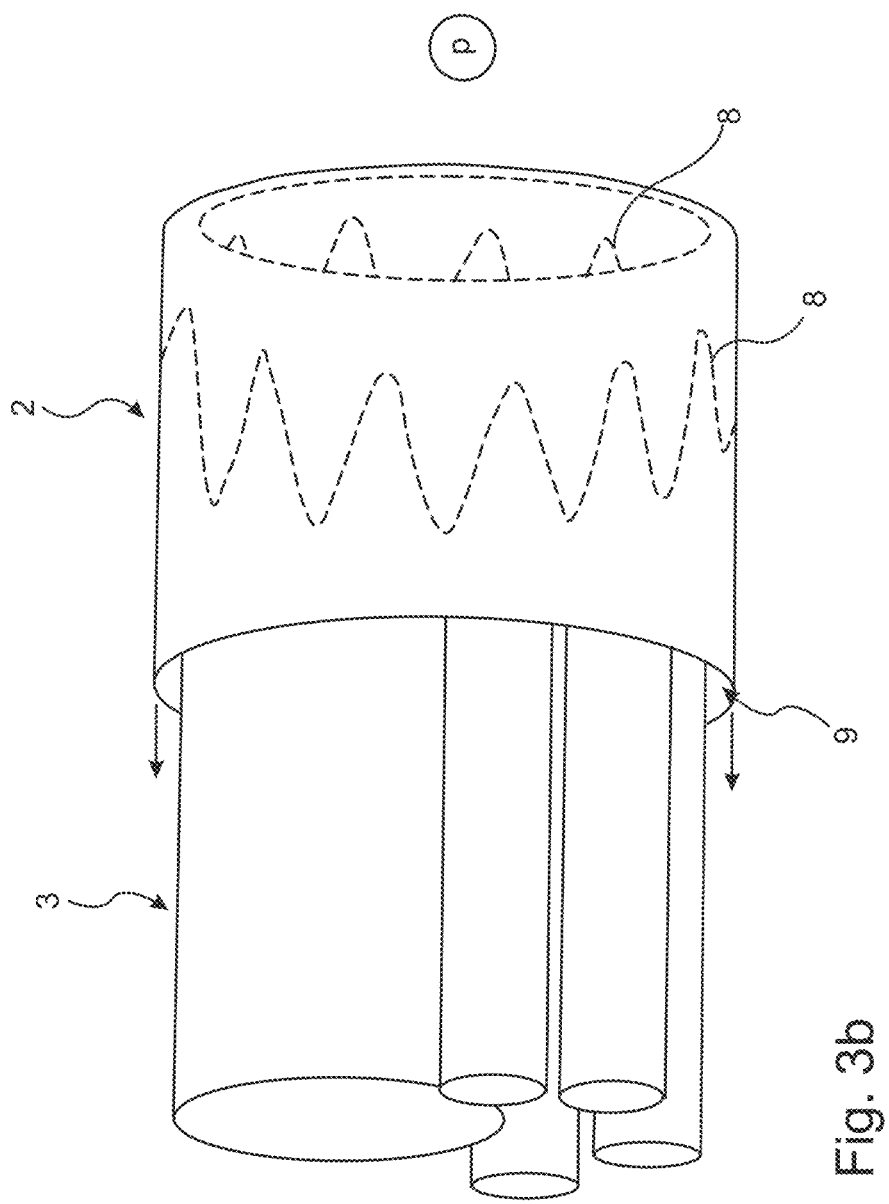
Figure 4B:
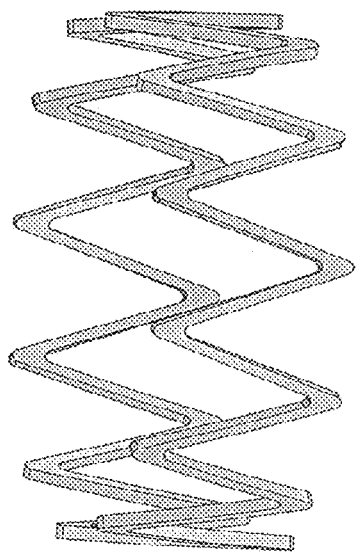
Figure 4A:
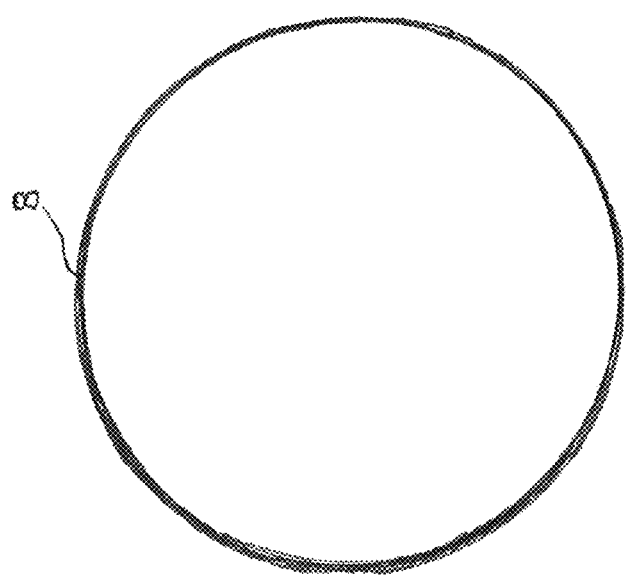
Figure 8:
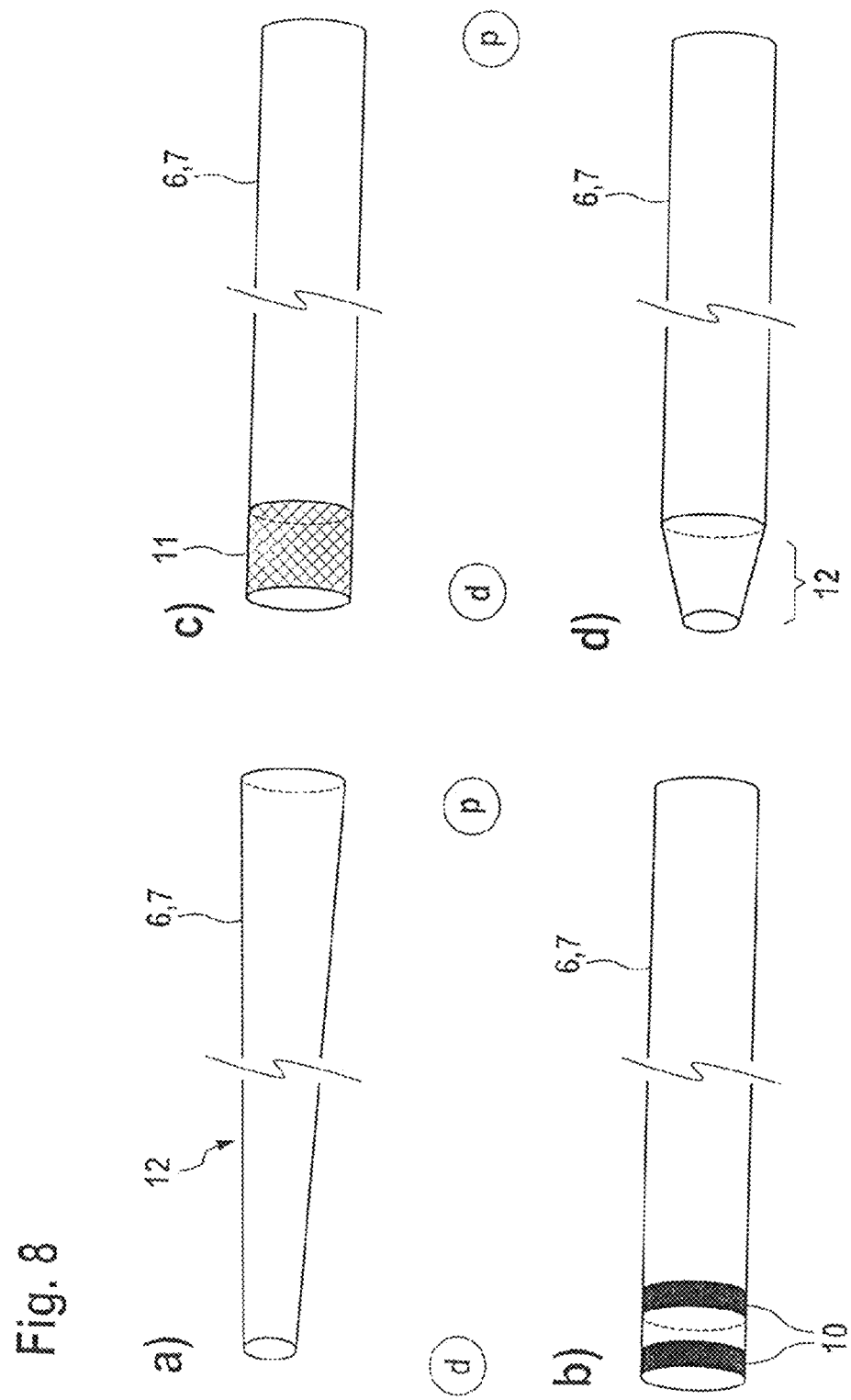
Figure 9:
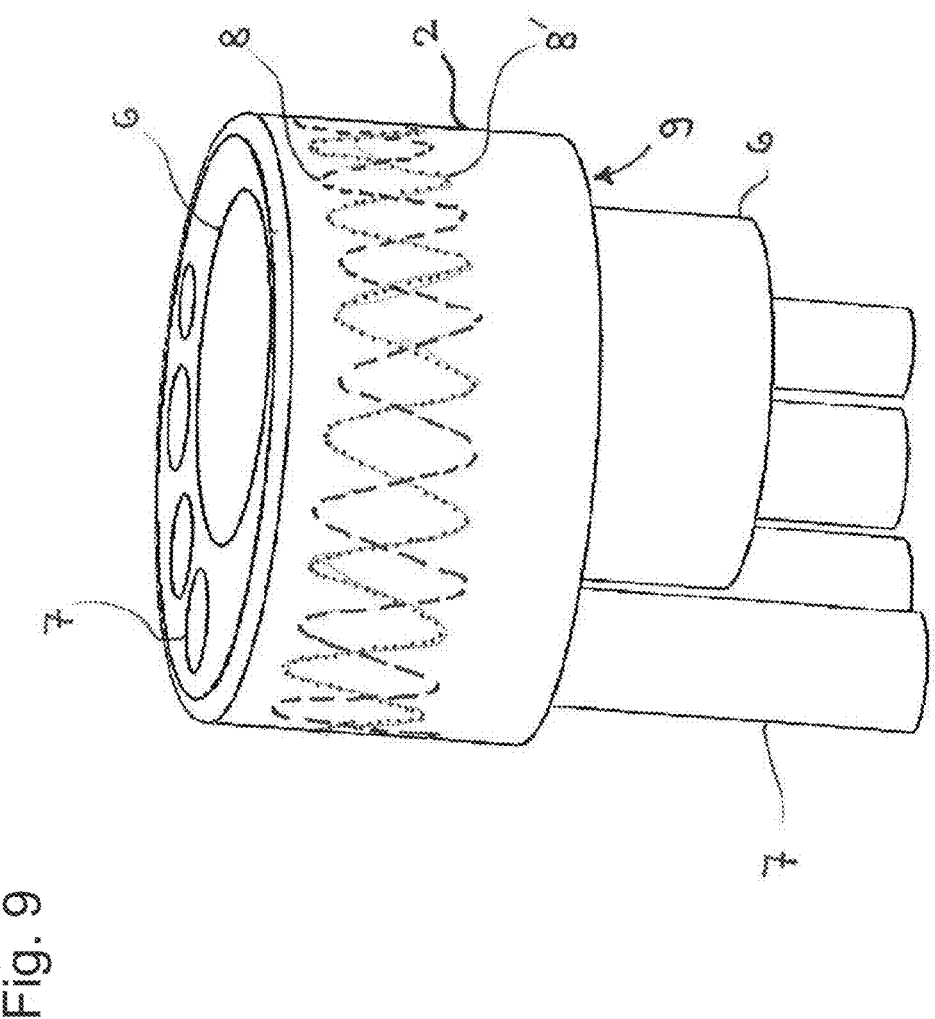

FIG. 3a-b illustrate a schematic representation of the folding of the proximal onto the distal section for a better understanding of a second embodiment of the inventive implant;

FIG. 4 illustrates a usable clamping ring proposed by the invention;

FIG. 5 is a schematic representation of a second embodiment of the implant proposed by the invention;

FIG. 6a-b show a transverse a) and a longitudinal section b) through a second embodiment of the implant according to the invention;

FIG. 7a-d show a schematic representation of possible distribution options of the distal lumina;

FIG. 8a-d show possible configurations of the distal ends of the branches for better fixation of the conveying stents; and FIG. 9 shows another embodiment.

Figure 1:
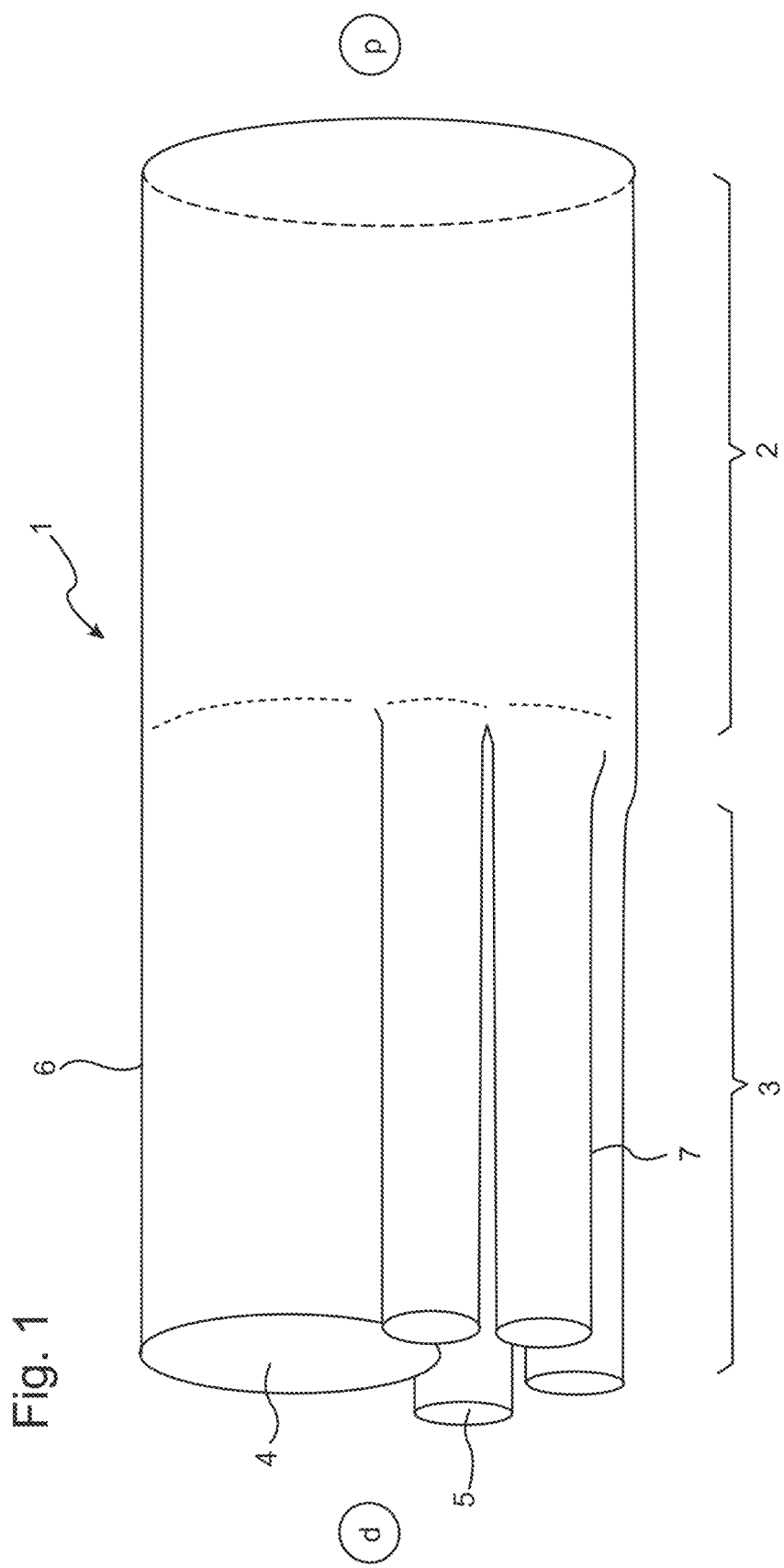
FIG. 1 shows a schematic representation of the tubular element.

FIG. 1 is a schematic representation of the tubular element 1 of an implant in accordance with the invention, said implant being divided into a proximal section 2 and a distal section 3. The proximal (p) single-lumen tubular element 1 branches distally (d) into at least two lumens 4, 5, with a preferred embodiment comprising one main lumen 4 and four secondary lumens 5, or correspondingly one large branch 6 and four smaller branches 7.

The relative proportions shown in this schematic representation have been selected purely with a view to making the individual parts to be easily recognizable. Accordingly, the ratio of proximal section 2 to the distal section 3 as well as the ratios of the individual distal lumens 4 and 5 or the lengths of the branches 6 and 7 may differ from what is shown in the figure.

Figure 2:
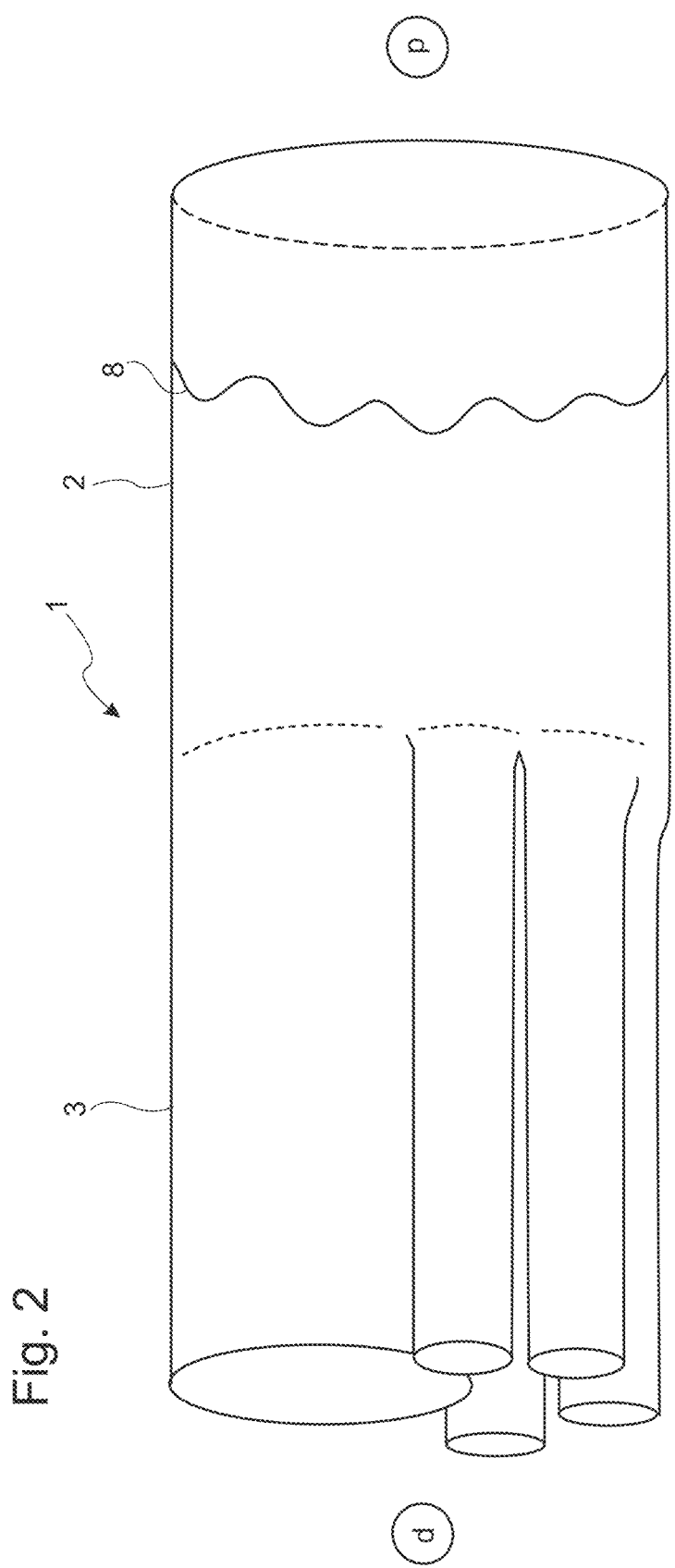
FIG. 2 is a schematic representation of a first embodiment of the implant proposed by the invention.

FIG. 2 illustrates the tubular element 1 shown in FIG. 1, with a clamping ring 8 being arranged for securing or fixation of the tubular element 1 in a vessel within the proximal section 2. In this embodiment, the clamping ring 8 is located in proximal section 2. If considered expedient, the proximal end of the tubular element 1 can project beyond the clamping ring 8 and be folded in-wards over the proximal end of the clamping ring into the lumen of the proximal section 2. Clamping ring 8 has an undulated shape.

FIGS. 3*a* and 3*b* indicate in general the arrangement of the proximal section 2 of the tubular element 1 in a first preferred embodiment. In this case, the proximal section 2 is folded over onto the distal section 3, so that the distal section 3 is finally at least partially encased by the proximal section 2. FIG. 3*b* shows the clamping ring 8 inserted into the space 9 of the folding of the proximal section, said ring having a zigzag configuration and being shown as a dashed line.

FIG. 4 shows a clamping ring 8 that can be used according to the invention in top view (a) and in perspective (b). In general, clamping ring 8 is a construct the coils of which are pressed together during the compression process, such as a wire ring or a tube cutout produced in a known manner with the help of a laser.

FIG. 5 depicts a preferred embodiment which is based on the folded over proximal section 2 as shown in FIGS. 3*a* and 3*b*. The proximal section 2 is folded over distally (d) up to the end of the branches 6, 7. Clamping ring 8 is arranged inside the folding 9 thus created. The lengths of the clamping ring 8, the proximal 2 and the distal section 3 are approximately the same in this illustration; the clamping ring 8 is completely arranged within the folding 9.

FIG. 6 shows a cross section 6*a* and a longitudinal section 6*b* through the preferred embodiment of the implant illustrated in FIG. 5. The dotted line indicates the clamping ring 8, the broken line the distal section 3 and the continuous line the proximal section 2 of the tubular element 1. As can be seen in both figures, the proximal section 2 is folded over to distal (d) and folded over inwardly to proximal around the clamping ring 8 located in the folding 9, so that clamping ring 8 is covered on all sides by the proximal section 2.

Figure 7:
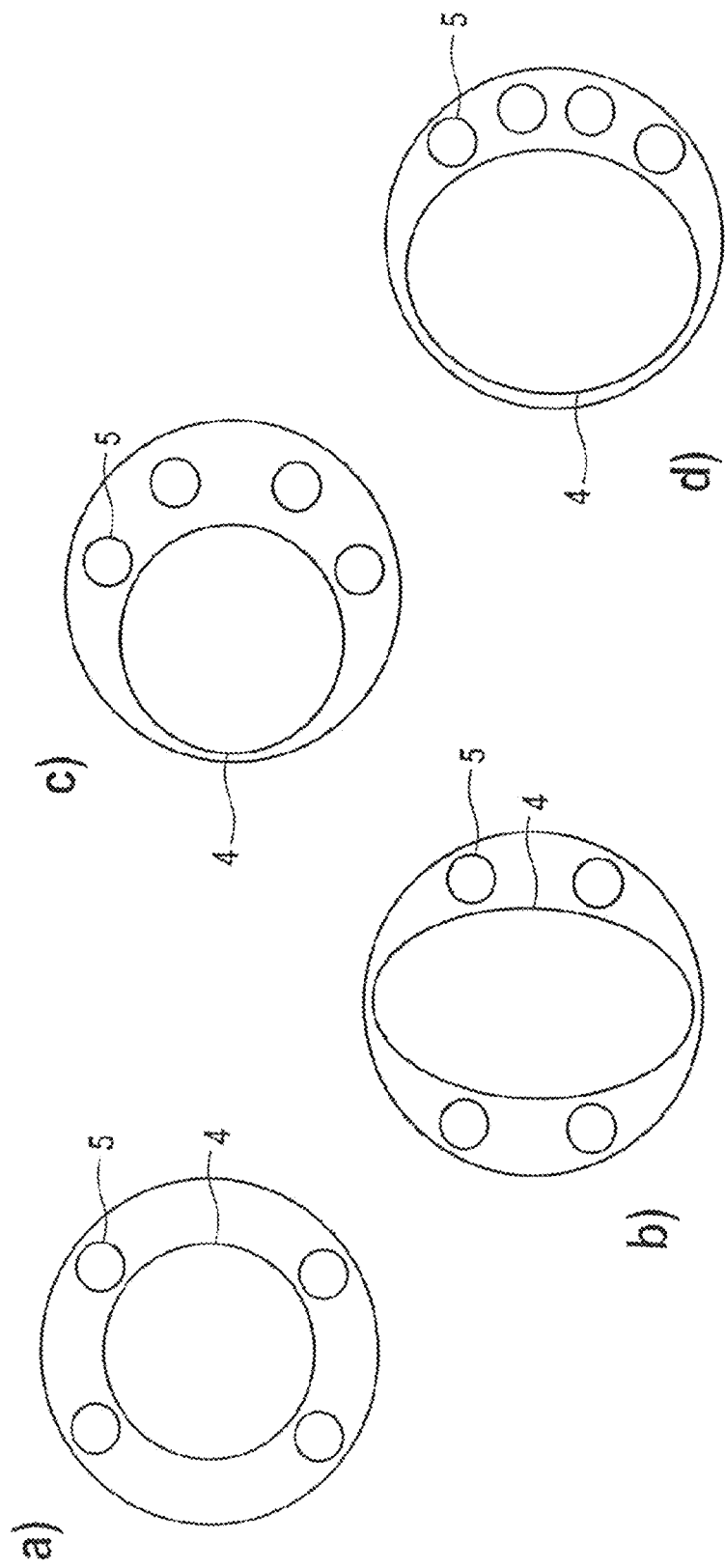

FIG. 7 is a schematic representation of cross sections through the implant, with different distributions and arrangements of the distal lumens 4, 5 being shown. The main lumen 4 can be arranged centrally (a, b) or eccentrically (c, d). The secondary lumens 5 can be arranged around the main lumen 4 (a, b) or on one side of it (c, d). In the cross sectional view, the main lumen 4 can be of round shape (a, c) or oval (b, d). Conceivable as well are embodiments in which the secondary lumens 5 also have an oval shape. A preferred embodiment is illustrated in FIG. 7*c*.

FIG. 8 shows various design options for the distal ends d of the distal branches 6, 7 for better fixation of the stents, which connect the distal branches 6, 7 with the respective vessels to be perfused. For this purpose and in a preferred embodiment, the distal branches may be tapered conically towards their end 12 entirely (a) or at the distal tip (d), at the tip they may have annular stabilizations 10 or a distally entirely reinforced structure 11 (c).

In FIG. 9 a version of the inventive implant is shown, in which two clamping rings 8 ensure that expansion takes place. The tubular element is divided into five lumina, one main lumen 6 and four secondary lumina 7. The proximal section 2 of the tubular element is folded over and forms a pocket/envelope 9, in which an outer clamping ring 8 (broken line) is arranged. A second clamping ring 8' is placed against it on the inside of the tubular element so that the radial forces exerted by the two clamping rings are combined. The inner and outer clamping ring 8 have a staggered arrangement, i.e. the wave peaks of the inner clamping ring 8' are located in the wave troughs of the outer clamping ring 8. Both clamping rings 8 can be connected to each other through the tubular element, for example by sewing.

LIST OF REFERENCE NUMERALS

1 Tubular element
2 Proximal section
3 Distal section
4 Main lumen
Secondary lumen
6 Main branch
7 Secondary branch
8 Clamping ring
9 Folding
Annular stabilization
11 Annular reinforcement
12 Taper
p Proximal
d Distal

The invention claimed is:

1. A multilumen implant for application in human and animal vascular systems/bodies, with a substantially tubular element (1) divided into a proximal (2) and a distal section (3), and a fixation element (8) for the fixation of the proximal section (2) in a target vessel, wherein the tubular element (1) branches into two or more lumens (4, 5) in the distal section (3), and wherein the fixation element (8) has a single clamping ring having an undulating shape that is meandering or zigzagging, arranged on the outside of the proximal section (2) of the tubular element (1), and wherein a free end of the proximal section (2) of the tubular element (1) facing away from the distal section (3) is folded around single clamping ring and embraces the single clamping ring in a pocket-like manner, and wherein a length of the free end of the proximal section (2) of the tubular element (1) that is folded around the single clamping ring corresponds to at least a length of the single clamping ring and wherein the two or more lumens (4, 5) in the distal section (3) are at least partially arranged inside the single clamping ring.

2. The multilumen according to claim 1, characterized in that the two or more lumens (4, 5) are a main lumen (4) and several secondary lumens (5).

3. The multilumen implant according to claim 2, characterized in that the secondary lumens (5) have a smaller caliber than the main lumen (4).

4. The multilumen implant according to claim 1, characterized in that the lumens (4, 5) of the distal section (3) of the tubular element (1) taper (12) in a distal direction.

5. The multilumen implant according to claim 1, characterized in that the lumens (4, 5) of the distal section (3) of the tubular element (1) have distal annular reinforcements (10, 11).

6. The multilumen implant according to claim 1, characterized in that the tubular element (1) is secured to the single clamping ring in particular by means of clamping, bonding/gluing, sewing or welding.

7. The multilumen implant according to claim 1, characterized in that the tubular element (1) consists of ePTFE.

8. The multilumen implant according to claim 7, characterized in that the tubular element (1) made of ePTFE is produced by electrospinning.

9. The multilumen implant according to claim 1, characterized in that the single clamping ring consists of a self-expanding material.

10. The multilumen implant according to claim 1, characterized in that the single clamping ring consists of a balloon-expanding material.

11. The multilumen implant according to claim 1, further comprising fastening elements for securing at least the proximal section (2) of the tubular element (1) to the vessel wall.

12. The multilumen implant according to claim 11, characterized in that the fastening elements are hooks and/or screws that are configured to extend into the vessel wall.

13. A kit comprising a multilumen implant according to claim 1, and a catheter for its implantation.

14. The kit according to claim 13, further comprising two or more stent grafts configured for connecting distal ends (6, 7) of the lumens (4, 5) to vessels.

* * * * *